United States Patent [19]

Gregonis et al.

[11] Patent Number: 4,557,724

[45] Date of Patent: * Dec. 10, 1985

[54] APPARATUS AND METHODS FOR MINIMIZING CELLULAR ADHESION ON PERITONEAL INJECTION CATHETERS

[75] Inventors: Donald E. Gregonis; Robert L. Stephen; Dennis L. Coleman, all of Salt Lake City; Stephen K. Hunter, Syracuse; Barry K. Hanover; Jeffrey J. Harrow, both of Salt Lake City, all of Utah

[73] Assignee: University of Utah Research Foundation, Salt Lake City, Utah

[*] Notice: The portion of the term of this patent subsequent to Aug. 23, 2000 has been disclaimed.

[21] Appl. No.: 522,914

[22] Filed: Aug. 12, 1983

Related U.S. Application Data

[63] Continuation-in-part of Ser. No. 235,185, Feb. 17, 1981, Pat. No. 4,405,305, which is a continuation-in-part of Ser. No. 200,830, Oct. 27, 1980, Pat. No. 4,400,167.

[51] Int. Cl.⁴ ............................................. A61M 25/00
[52] U.S. Cl. ......................................... 604/49; 604/93; 604/265
[58] Field of Search ............... 604/93, 891, 51, 174, 604/175, 48, 49, 50, 8–10, 29, 73, 117, 132, 181, 185, 265, 266, 246, 257, 280

[56] References Cited

U.S. PATENT DOCUMENTS

| | | | |
|---|---|---|---|
| 3,137,299 | 6/1964 | Tabor | 128/351 |
| 3,310,051 | 3/1967 | Schulte | 128/216 |
| 3,396,727 | 8/1968 | Mount | 128/349 |
| 3,540,451 | 11/1970 | Zeman | 128/334 |
| 3,580,983 | 5/1971 | Jackson | 174/47 |
| 3,633,585 | 1/1972 | McDonald, Jr. | 128/348 |

(List continued on next page.)

FOREIGN PATENT DOCUMENTS

| | | |
|---|---|---|
| 7715107 | 12/1978 | France . |
| 2056282 | 3/1981 | United Kingdom . |
| 2072514 | 10/1981 | United Kingdom . |
| 2073024 | 10/1981 | United Kingdom . |

OTHER PUBLICATIONS

Fox, Jr. et al., "Mechanism of Silver Sulfadiazine Action on Burn Wound Infections," *Antimicrobial Agents and Chemotherapy,* 5:582–588, (U.S.A.; Jun. 1974).

Felig, "Insulin: Rates and Routes of Delivery," *New England Journal of Medicine,* 291:103–104, (U.S.A., 1974).

(List continued on next page.)

*Primary Examiner*—C. Fred Rosenbaum
*Assistant Examiner*—Mario Costantino
*Attorney, Agent, or Firm*—Workman, Nydegger & Jensen

[57] ABSTRACT

The present invention is directed to a subcutaneous peritoneal injection catheter apparatus and methods which minimizes catheter obstruction during use. The apparatus includes a receiving chamber or reservoir having a relatively small internal volume while employing a penetrable membrane and relatively enlarged target surface area. The reservoir is interconnected with the peritoneal cavity by a hollow stem. The penetrable membrane accommodates a hollow needle being inserted into the receiving reservoir and is configurated with a dome-like profile so that the membrane may also be depressed to expel insulin from the receiving reservoir into the peritoneal cavity in a direction generally toward the mesenteric peritoneal membrane.

The portion of the apparatus which is in the peritoneal cavity is preferably constructed of, or coated with, a material which is capable of minimizing the adhesion of cells and the growth of bacteria on that portion of the apparatus. In a presently preferred embodiment of the subcutaneous peritoneal injection catheter, the portion of the catheter to be within the peritoneal cavity is constructed of a polyurethane material, and this polyurethane material is then coated with a solution of polyurethane and poly(ethylene glycol) in a suitable solvent.

33 Claims, 3 Drawing Figures

U.S. PATENT DOCUMENTS

| | | | |
|---|---|---|---|
| 3,640,269 | 2/1972 | Delgado | 128/2 R |
| 3,765,414 | 10/1973 | Arlen | 128/260 |
| 3,783,868 | 1/1974 | Bokros | 604/891 |
| 3,815,577 | 6/1974 | Bucalo | 128/1 R |
| 3,818,511 | 6/1974 | Goldberg et al. | 3/1 |
| 3,861,396 | 1/1975 | Vaillancourt et al. | 604/265 |
| 3,927,242 | 12/1975 | Rembaum et al. | 428/341 |
| 4,026,296 | 5/1977 | Stoy et al. | 604/96 |
| 4,054,139 | 10/1977 | Crossley | 128/260 |
| 4,160,454 | 7/1979 | Foux | 128/348 |
| 4,184,497 | 1/1980 | Kolff et al. | 131/213 |
| 4,190,040 | 2/1980 | Schulte | 128/1 R |
| 4,190,048 | 2/1980 | Sampson | 128/215 |
| 4,220,153 | 9/1980 | Dresback | 604/892 |
| 4,253,463 | 3/1981 | Kim | 128/348 |
| 4,256,102 | 3/1981 | Monaco | 128/213 |
| 4,368,737 | 1/1983 | Ash | 604/175 |
| 4,400,169 | 8/1983 | Stephen | 604/49 |
| 4,400,169 | 8/1983 | Stephen | 604/49 |
| 4,405,305 | 9/1983 | Stephen et al. | 604/49 |
| 4,411,795 | 10/1983 | Olson | 210/679 |
| 4,490,137 | 12/1984 | Moukheibir | 604/28 |

OTHER PUBLICATIONS

Karanicolas et al., "Home Peritoneal Dialysis: 3 Years' Experience in Toronto," *CMA Journal*, 116:266–269, (Canada, Feb. 5, 1977).

S. Nagoaka et al., "Interaction Between Blood Components and Hydrogels With Poly(oxyethylene) Chain," *J. Biomed Materials Research*, vol. 16, pp. 209–217, (1982).

C. Beauchamp et al., "A New Procedure for the Synthesis of Polyethylene Glycol-Protein Adducts; Effects on Function, Recptor Recognition, and Clearance of Superoxide Dismutase, Lactoferrin, and $\alpha_2$-Macroglobulin," *Analytical Biochemistry*, vol. 131, pp. 25–33, (1983).

Y. Mori et al., "A New Antithrombogenic Material With Long Polyethyleneoxide Chain," *Trans. Am. Soc. Artif. Intern. Organs*, vol. 28, pp. 459–463, (1982).

E. W. Merrill et al., "Platelet-Compatible Hydrophilic Segmented Polyurethanes From Polyethylene Glycols and Cyclohexane Diisocyanate," *Trans. Am. Soc. Artif. Intern. Organs*, vol. 28, pp. 482–487, (1982).

S. Nagaoka et al., "Interaction Between Blood Components and Hydrogels With Poly(oxyethylene) Chain," *Polymer Preprints*, vol. 24, pp. 67–68, Mar. (1983).

T. Matsuda and T. Akutsu, "In Vitro and In Vivo Assessment of Blood/Material Interactions of Hydrophobic Segmented Polyurethanes," *Abstract of the Seattle American Chemical Society Meeting*, (Mar. 1983).

Y. Gnanou et al., "Hydrophilic Polyurethane Networks Based on Poly(ethylene oxide): Synthesis, Characterization, and Properties, Potential Applications as Biomaterials," *Macromolecules*, vol. 17, pp. 945–952, (1984).

B. Whicher and J. Brash, "Platelet-Foreign Surface Interactions; Release of Granule Constituents from Adherent Platelets," *J. Biomed. Materials Research*, vol. 12, pp. 181–201, (1978).

Merrill et al., "The Use of an Inlying Plastic Conduit for Chronic Peritoneal Irrigation," *Trans. Amer. Artif. Inter. Organs*, 8:252–255, (1962).

Boen et al., "Periodic Peritoneal Dialysis in the Management of Chronic Uremia," *Trans. Amer. Soc. Artif. Inter. Organs*, 8:256–262, (1962).

Barry et al., "A New Flexible Cannula and Seal to Provide Prolonged Access to the Peritoneal Cavity for Dialysis," *Trans. Amer. Soc. Artif. Inter. Organs*, 9:105–107, (1963).

Henderson et al., "Further Experience with the Inlying Plastic Conduit for Chronic Peritoneal Dialysis," *Trans. Amer. Soc. Artif. Inter. Organs*, 9:108–116, (1963).

Palmer et al., "Prolonged Peritoneal Dialysis for Chronic Renal Failure," *The Lancet*, 1:700–702, (1964).

Malette et al., "A Clinically Successful Subcutaneous Peritoneal Access Button for Repeated Peritoneal Dialysis," *Trans. Amer. Soc. Artif. Organs*, 10:396–398, (1964).

Moyer et al., "Treatment of Large Human Burns With 0.5% Silver Nitrate Solution," *Archives of Surgery*, 90:812–867, (Jun. 1965).

Jacob et al., "Repeated Peritoneal Dialysis by the Catheter Replacement Method: Description of Technique and a Replaceable Prosthesis for Chronic Access to the Peritoneal Cavity," *Proc. EDTA*, (1967), pp. 136–140.

Fox, Jr., "Silver Sulfadiazine–A New Topical Therapy for Pseudomonas in Burns," *Archives of Surgery*, 96:184–188, (Feb. 1968).

Tenckhoff et al., "A Bacteriologically Safe Peritoneal Access Device," *Trans. Amer. Soc. Artif. Inter. Organs*, 14:181–186, (1968).

Brewer et al., "Indwelling Peritoneal (Tenckhoff) Dialysis Catheter," *JAMA*, vol. 219, No. 8, pp. 1011–1015, (Feb. 21, 1972).

Modak et al., "Binding of Silver Sulfadiazine to the Cellular Components of Pseudomonas Aeruginosa," *Biochemical Pharmacology*, 22:2391–2404, (Great Britain, 1973).

Fox, Jr. et al., "Topical Chemotherapy for Burns Using Cerium Salts and Silver Sulfadiazine," *Surgery, Gynecology, & Obstetrics*, 144:668–672, (May, 1977).

Oreopoulos, "Renewed Interest in Chronic Peritoneal Dialysis," *Kidney International*, vol. 13, Supp. 8, pp. S-117 to S-119, (1978).

Klempner, "Interpenetrating Polymer Networks," *Angew. Chem. Int. Ed. Engl.*, 17:97–106, (1978).

Nolph, "Effects of Intraperitoneal Vasodilators on Peritoneal Clearances," *Proceedings 11th Ann. Contractors' Conference*, (1978), pp. 29–33.

Schade et al., "The Intravenous, Intraperitoneal, and Subcutaneous Routes of Insulin Delivery in Diabetic Man," *Diabetes*, 28:1069–1072, (1979).

Fox, Jr. et al., "Metal Sulfonamides as Antibacterial Agents in Topical Therapy," *Scand. J. Plast. Reconstr. Surg.*, 13:89–95, (1979).

"Guidelines for Physiochemical Characterization of Biomaterials," *Report of the National Heart, Lung, and Blood Institute Working Group*, (1979), pp. 56–59.

Ash et al., "The Column Disc Peritoneal Catheter: A Peritoneal Access Device with Improved Drainage," *ASAIO Journal*, 3:109–115, (Jul./Sep., 1980).

Schade et al., "Normalization of Plasma Insulin Profiles with Intraperitoneal Insulin Infusion in Diabetic Man," *Diabetologia*, 19:35–39, (1980).

Kablitz et al., "Subcutaneous Peritoneal Access Device (List continued on next page.)

OTHER PUBLICATIONS

Used for Intraperitoneal Insulin Treatment of Non-uraemic Diabetic Patients," *Proceedings of the Second International Symposium on Peritoneal Dialysis*, (1981), pp. 170–172.

Stephen et al., "Long-Term Intraperitoneal Insulin Treatment: Preliminary Studies in 12 Diabetic Patients," *Diabetic Renal-Retinal Syndrome*, 2:447–461, (1982).

Smith et al., "Surface Oxidation of Cis-Trans Polybutadiene," *J. Appl. Polymer Science*, 26:1269–1276, (1982).

Stephen et al., "Stabilization and Improvement of Renal Function in Diabetic Nephropathy," *Diabetic Nephropathy*, 1:8–13, (1982).

Felig, *Diabetes Its Physiological and Biochemical Basis*, pp. 100–103, (U.S.A., 1980).

APPARATUS AND METHODS FOR MINIMIZING CELLULAR ADHESION ON PERITONEAL INJECTION CATHETERS

RELATED APPLICATIONS

The present application is a continuation-in-part of application Ser. No. 235,185, filed Feb. 17, 1981 (now U.S. Pat. No. 4,405,305), which is a continuation-in-part of application Ser. No. 200,830, filed Oct. 27, 1980 (now U.S. Pat. No. 4,400,169).

BACKGROUND

1. The Field of the Invention

This invention relates to peritoneal injection catheters and, more particularly, to a novel apparatus and method for minimizing obstruction of subcutaneous peritoneal injection catheters during use.

2. The Prior Art

A large proportion of the various chemical reactions that occur in the body are concerned with making energy in foods available to the various physiological systems in the cells. Metabolism of glucose is particularly important in many of these chemical reactions, and the body has a very sophisticated regulatory system adapted to maintain blood glucose levels at an optimum level so that adequate amounts of glucose will be available as needed.

One of the most important elements in the glucose regulatory system is the hormone "insulin." Insulin is a relatively small protein, having a molecular weight of only 5743 daltons; it is comprised of two amino acid chains connected by a pair of disulfide linkages.

Insulin has the ability to regulate glucose metabolism in two ways. First, insulin has the ability to increase the rate of glucose transport through the cell membrane of many types of cells in the body. In the absence of insulin, the rate of glucose transport into these cells is reduced to less than one-fourth of the normal rate. On the other hand, excessive levels of insulin can increase the rate of glucose transport to nearly five times normal. Adjustments in the level of insulin in the body can thus be seen to have the capability of adjusting the rate of glucose absorption by twenty fold.

In addition to its role in glucose transport, insulin also acts as a regulatory hormone. Normally, when digestion results in rising levels of glucose in the body, certain cells in the pancreas, known as "beta cells" of the "islets of Langerhans," commence secreting insulin into the portal vein. About half of the secreted insulin is immediately absorbed by the liver, with the remaining portion being distributed through most of the rest of the body.

In response to the rising level of insulin, the liver produces large quantities of an enzyme known as glucokinase, which causes conversion of glucose into glycogen which is then stored. Importantly, a large portion of the excess glucose entering the blood system as a product of digestion is rapidly removed by the liver in order to maintain relatively normal concentrations of glucose in the bloodstream.

Later, when the blood glucose level commences to drop below normal, the pancreas reduces its secretion of insulin, and the "alpha cells" of the islets of Langerhans commence to secrete a hormone known as "glucagon." Glucagon stimulates the conversion of glycogen in the liver into glucose by activating another enzyme known as liver phosphorylase. This, in turn, results in release of glucose into the bloodstream for transport throughout the body.

From the foregoing, it will be appreciated that the pancreas and the liver play a major role in regulating the level of glucose in the bloodstream. Unfortunately, the delicate balance between the actions of the pancreas and the liver can be easily upset. For example, it is not uncommon for the pancreas to suffer damage so that it no longer secretes adequate levels of insulin. This condition is known as "diabetes mellitus," or more commonly, simply "diabetes." Serious cases of diabetes often exhibit a total cessation of insulin secretion.

As would be expected, insufficient secretion of insulin substantially reduces the transport of glucose into most tissues of the body. (The most notable exception is the brain; glucose transport across the blood-brain barrier is dependent upon diffusion rather than insulin-mediated transport.) Further, the glucose regulatory function is also impaired since, in the absence of insulin, little glucose is stored in the liver during times of excess and, hence, is not available for subsequent release in times of glucose need.

One result of the lack of sufficient quantities of insulin in the body is a rise in the blood glucose concentration. This causes the osmotic pressure in extracellular fluids to rise above normal, which in turn often results in significant cellular dehydration. This problem is exacerbated by the action of the kidneys which act to remove excessive qantities of glucose from the blood; the increase in glucose concentration in the kidneys cause yet additional fluids to be removed from the body. Thus, one of the significant effects of diabetes is the tendency for dehydration to develop.

However, an even more serious effect occurs because of the failure of body tissues to receive adequate levels of glucose. In the absence of adequate levels of glucose, the metabolism of body cells switches from carbohydrate metabolism to fat metabolism. When the body is required to depend heavily upon fat metabolism for its energy, the concentration of acetoacetic acid and other keto acids rises to as much as thirty times normal, thus causing a reduction in the pH of the blood below its normal pH level of 7.4.

Again, this problem is exacerbated by the kidneys. Substantial quantities of the keto acids combine with the basic ion sodium. Then, as the kidneys remove the various keto acids from the blood, substantial amounts of sodium are also lost, thereby resulting in even further decreases in blood pH. If the blood pH is reduced to below about 7.0, the diabetic person will enter a state of coma; and this condition is usually fatal.

The generally accepted treatment for diabetes is to administer enough insulin so as to restore carbohydrate metabolism. Traditionally, administration of insulin has been made by injections into the peripheral circulation, either from an intramuscular or subcutaneous injection. Although widely used, this form of treatment has several disadvantages.

First, using peripheral insulin administration, only about ten percent of the administered insulin reaches the liver, as compared to approximately fifty percent in normal persons. As a consequence, hepatic glucose production is not first reduced; rather, blood glucose is lowered by increased utilization by other tissues (such as muscle and fat), due to the presence of high levels of insulin in the peripheral circulation. Hence, normal levels of blood sugar are achieved only by carefully matching any increased peripheral utilization of blood sugar to an increased hepatic production. This in inherently much more difficult than simply decreasing hepatic glucose production.

Additionally, these traditional administration methods fail to provide the type of control over the blood glucose concentration that occurs in a normal person. Clearly, once- or twice-daily injections of insulin cannot supply controlled variable amounts of insulin in response to changing metabolic demands during the course of the day. Hence, when using traditional insulin administration methods, the blood glucose content tends to fluctuate between abnormally high and low concentrations. Significantly, there are some indications that such periodic rise and fall of glucose concentrations between hyperglycemia and hypoglycemia contributes to devastating vascular and neurological complications over a period of time. (It is not uncommon, for example, for a long-term diabetic to experience atherosclerosis, arteriosclerosis, hypertension, severe coronary heart disease, retinopathy, cataracts, chronic renal disease, or loss of the extremities.)

Another consequence of massive injections of insulin on a periodic basis is that excessive amounts of insulin occasionally enter the bloodstream, thereby causing glucose to be rapidly transported into the cells and decreasing the blood glucose to substantially below normal levels. Unfortunately, diabetic patients already have little glucose reserve, since the liver, in its state of underinsulinization, is already releasing glucose. Consequently, the blood sugar level will plummet despite adequate levels of counterregulatory hormones (such as glucagon, epinephrine, norepinephrine, and growth hormones), which normally would increase liver production of glucose in emergency situations.

Importantly, if the blood glucose level is reduced too much, there will be insufficient glucose to diffuse across the blood-brain barrier, and the brain and central nervous system will begin to suffer from depressed metabolism. This hypoglycemic reaction (having a progression of symptoms from nervousness, sweating, stupor, and unconsciousness to occasionally irreparable brain damage), will occur until sugary substances are taken either by mouth or intravenously.

The resulting ongoing cycle between hyperglycemia and hypoglycemia has created a basic rift in the philosophy of diabetic control. The "tight control" philosophy claims that the long-term devastations of diabetes (that is, blindness, heart attacks, kidney failure, and loss of extremities), are due to abnormally elevated sugar levels. Those ascribing to this "tight control" philosophy strive to keep blood sugar within the normal range even at the risk of frequent (more than once a week) hypoglycemic reactions. The converse "loose control" philosophy is based upon the presumption that the basic premise of the "tight control" philosophy has yet to be proved and that the considerable risks of hypoglycemic reactions are not worth an unproved benefit.

In an effort to avoid the undesirable effects of the traditional insulin administration methods, various closed and open loop control delivery systems have been developed. Closed loop delivery systems are synonymous with prolonged hospitalization. Additionally, they are awkward to wear, they require tubing sets and implanted needles and, in spite of claims made to the contrary, they can malfunction ("surge"), usually at the most inconvenient hours.

Open loop delivery systems, on the other hand, actually produce a more sustained, if somewhat better regulated, hyperinsulinemic state. However, the therapists involved still persist in using both open and closed loop systems to deliver insulin peripherally, thereby giving rise to many of the difficulties already mentioned.

Consequently, due to the problems and difficulties set forth above, those skilled in the art of treating diabetes have sought to find improved methods for administering therapeutic insulin to diabetic individuals. Perhaps one of the most promising insulin administration methods which is currently being investigated comprises the administration of insulin via the peritoneum.

The peritoneum is the largest serous membrane in the body and consists (in the male) of a closed sac, a part of which is applied against the abdominal parietes, while the remainder is reflected over the contained viscera. (In the female, the peritoneum is not a closed sac, since the free ends of the uterine tubes open directly into the peritoneal cavity.)

The part of the peritoneum which lines the abdominal wall is named the parietal peritoneum and that which is reflected over the contained viscera constitutes the mesenteric (visceral) peritoneum. The space between the perietal and mesenteric layers of the peritoneum is called the peritoneal cavity. However, under normal conditions, this "cavity" is merely a potential one, since the parietal and mesenteric layers are typically in contact.

Of particular significance, a portion of the blood circulation of the peritoneum leads directly into the portal venous system. Hence, any insulin absorbed by the peritoneum would potentially have nearly direct access to the liver. As a result, such insulin would first be available to reduce hepatic glucose production, and the insulin could, therefore, potentially function more effectively in its glucose regulatory capacity.

For a number of years, it has been well-known that the peritoneal membrane will function fairly effectively as an exchange membrane for various substances. Thus, as early as 1923, peritoneal dialysis was first applied clinically. At the present time, peritoneal dialysis is being used with increasing frequency to treat individuals suffering from end-stage renal disease.

In a typical peritoneal dialysis treatment, approximately two liters of dialysate is infused into the peritoneal cavity. Then, after the dialysate has remained within the peritoneal cavity for a period of time, thereby permitting the necessary diffusion across the peritoneal membrane, the dialysate is removed. This procedure is typically repeated a number of times during each dialysis treatment. Thus, in simple terms, the peritoneal cavity, together with the dialysate, functions as an artificial kidney.

The performance of peritoneal dialysis necessarily requires some type of peritoneal access device. The first peritoneal access device was a piece of rubber tubing temporarily sutured in place. By 1960, peritoneal dialysis was becoming an established form of artificial kidney therapy; and, in order to lessen the discomfort of repeated, temporary punctures into the peritoneal cavity, various access devices permitting the painless insertion of acute or temporary peritoneal catheters were developed.

The most common peritoneal access device is of the Tenckhoff type in which a capped, percutaneous, silastic tube passes through the abdominal wall into the peritoneal cavity. Another peritoneal access device (the "Gottloib" prosthesis) consists of a short, "golf tee" shaped device which is adapted to be placed under the skin with a hollow tubular portion extending just into the peritoneal cavity. This device is designed specifically to allow the insertion of an acute peritoneal catheter (or trocar) through the skin and down through this access tubing directly into the peritoneal cavity.

Another device consists of a catheter buried underneath the skin and extending into the peritoneal cavity via a long tubing. Peritoneal dialysis is performed by inserting a large needle into the subcutaneous portion of the catheter.

When using such access devices, a variety of drugs or other fluids have sometimes been added to the large volumes of peritoneal dialysis solutions and instilled into the peritoneal cavity for various therapeutic reasons. Some examples of these drugs are antibiotics, amino acids, and insulin. However, such therapeutic maneuvers are merely fortuitous, in that the clinician is simply taking advantage of a particular situation, that is, a peritoneal access device implanted in a particular group of patients. Importantly, there are cogent reasons for not using existing, permanent peritoneal access devices for simple drug injections in a wide variety of patients not suffering from end-stage renal disease.

First, the majority of prior art peritoneal access devices are long, clumsy, percutaneous, infection-prone silastic tubes. Hence, it is undesirable that any patient would wear such a device on a permanent or semi-permanent basis, unless it is absolutely necessary.

In addition, most of the prior art peritoneal access devices have a relatively large internal volume, that is, relatively large volumes of fluid are required in order to fill the devices. As mentioned above, during a typical dialysis treatment, approximately two liters of dialyzing fluid is injected into the peritoneal cavity at one time. Thus, when existing devices are used for purposes of peritoneal dialysis, the relatively large internal volume of the device is of little consequence. However, when injecting small quantities of fluid or drugs into the peritoneal cavity, this volume is a very real hindrance since the injected fluid may simply remain within the device itself instead of entering the peritoneal cavity.

Further, it has been found that bacteria will sometimes accumulate and grow within the prior art access devices. Also, the prior art peritoneal access devices often become obstructed by body cells and/or bacteria after they are implanted in a patient. In many cases, such obstruction cannot be eliminated without damaging the device, and the access device must, therefore, be removed.

Accordingly, it would be an improvement in the art to provide a peritoneal catheter apparatus which can be used to inject small volumes of fluid into the peritoneal cavity and which would minimize the accumulation or adhesion of body cells on the catheter. In addition, it would be an improvement in the art to provide an apparatus and method for minimizing the occurrence of tissue growth on or in a peritoneal injection catheter. Such devices and methods are disclosed and claimed herein.

BRIEF SUMMARY AND OBJECTIONS OF THE INVENTION

The present invention relates to a novel subcutaneous peritoneal injection catheter apparatus and method which minimizes cellular adhesion during use.

The apparatus includes a receiving chamber or reservoir having a relatively small internal volume while employing a penetrable membrane and relatively enlarged target surface area. The reservoir is interconnected with the peritoneal cavity by a hollow stem. the penetrable membrane accommodates a hollow needle being inserted into the receiving reservoir and is configurated with a dome-like profile so that the membrane may also be depressed to expel insulin from the receiving reservoir into the peritoneal cavity in a direction generally toward the mesenteric peritoneal membrane.

The portion of the apparatus which is in the peritoneal cavity is preferably constructed of, or coated with, a material which is capable of minimizing the adhesion of cells and the growth of bacteria on that portion of the apparatus. In a presently preferred embodiment of the subcutaneous peritoneal injection catheter, the portion of the catheter to be within the peritoneal cavity is constructed of a polyurethane material. This polyurethane material is then coated with a solution of polyurethane and poly(ethylene glycol) in a suitable solvent.

It is, therefore, a primary object of this invention to provide an improved implantable peritoneal injection catheter which minimizes the adhesion and accumulation of cells on the surfaces of the catheter.

Another object of this invention is to provide an improved implantable peritoneal injection catheter which minimizes tissue growth on the surfaces of the catheter.

It is a further object of this invention to provide a method for minimizing such cellular adhesion, and still maintain the structural integrity of the peritoneal catheter.

Finally, it is an object of this invention is to provide an improved implantable subcutaneous peritoneal injection catheter which may be used by a single patient over a relatively long period of time without interruption or malfunction.

These and other objects and features of the present invention will become more fully apparent from the following description and appended claims taken in conjunction with the accompanying drawings.

DETAILED DESCRIPTION OF THE PREFERRED EMBODIMENTS

Figure 1:
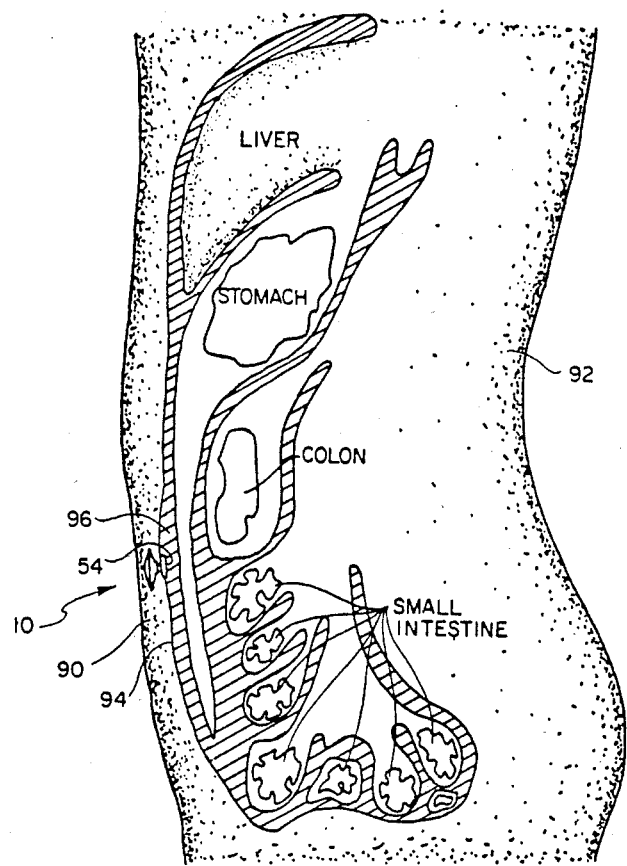
FIG. 1 is a schematic illustration of a subcutaneous peritoneal injection catheter shown implanted in the abdominal wall of a torso.

This invention comprises an improvement to subcutaneous peritoneal injection catheters for using in injecting drugs or other fluids into the peritoneal cavity.

General Discussion

As an alternative to both intravenous and intramuscular insulin delivery, portal venous administration of insulin has given highly encouraging results in experimental animals; less insulin is required to achieve normoglycemia and hyperinsulinemia is avoided. Long-term access directly into the portal system, however, carries several severe risks, all of which are lethal.

Nevertheless, there is a secondary and much safer route leading directly into the portal venous system—the mesenteric (visceral) peritoneal membrane. Although access to the intraperitoneal site is more difficult, it has the potential advantages of avoiding peripheral hyperinsulinemia, insulinizing the liver via direct portal venous system insulin absorption, and more rapid absorption than subcutaneously delivered insulin.

As alluded to above, when administering insulin via the peritoneum, it is most desirable that the insulin be substantially absorbed by the mesenteric, rather than the parietal, peritoneal membrane. If the insulin is absorbed by the parietal peritoneal membrane, the insulin enters the body's general systemic venous system. The effect is thus the same as if the insulin has been injected intramuscularly; that is, the insulin is gradually absorbed into the peripheral circulatory system and only a portion of the insulin reaches the liver. As a result, control of glycemia is not significantly better than that achieved usually conventional intramuscular injections. If the injected insulin is absorbed by the mesenteric peritoneal membrane, on the other hand, the insulin is absorbed into the portal venous system and made readily available to the liver.

Preliminary results of experiments using intraperitoneal delivery of insulin appear favorable. Insulin delivery into the peritoneum is reported to have resulted in a rapid rise in circulating peripheral insulin concentration, which peaked at 30-45 minutes following the initiation of insulin delivery. Furthermore, when the infusion rate of intraperitoneal insulin was reduced to the background rate, a gradual decline in peripheral insulin concentration to normal fasting values resulted. (This free insulin response is a marked contrast to the continuing high levels following intramuscular insulin injection.)

It was, therefore, concluded that normalization of plasma insulin profiles was achievable with intraperitoneal infusion of insulin and, further, that meal-related hyperglycemia (elevated blood glucose) is well-controlled with intraperitoneal insulin and yet hypoglycemic episodes are reduced compared to subcutaneous delivery. See, D. S. Schade, R. P. Eaton, N. M. Friedman, & W. J. Spencer, "Normalization of Plasma Insulin Profiles With Intraperitoneal Insulin Infusion in Diabetic Man," 19 DIABETOLOGIA 35-39 (1980).

Intraperitoneal delivery of insulin has been performed in ketosis-prone diabetic human subjects on a short-term basis (i.e., a matter of hours). Such intraperitoneal delivery achieves comparable glycemic control to that achieved with intramuscular insulin, with only approximately half the integrated blood levels of plasma insulin. Intraperitoneal insulin has also been utilized long term in patients with ketosis-prone diabetes and end-stage renal disease who were being treated by continuous ambulatory peritoneal dialysis. Adequate control was achieved in the three patients reported.

There appears to be no conclusive documentation substantiating the thesis that the intraperitoneal delivery of drugs is primarily absorbed into the portal venous system (mesenteric peritoneum) rather than the general systemic venous system (parietal peritoneum). However, there is a considerable amount of indirect evidence for this hypothesis: (1) at laparatomy one's field of vision is virtually totally obscured by the mesenteric peritoneum; (2) the work of other researchers indicates that control of glycemia by intraperitoneal insulin administration is good, even though there was a 50% "loss" of insulin—presumably picked up by the liver before reaching the peripheral circulation; and (3) intraperitoneal administration of sodium nitroprusside (for the purpose of causing intraperitoneal vasodilatation) results in no detectable levels of peripheral plasma thiocyanate. (It is assumed that metabolism of nitroprusside by the liver accounted for the lack of peripheral thiocyanate.)

A peritoneal injection catheter developed by the Division of Artificial Organs at the University of Utah have, inter alia, the following features: (1) the internal volume of the device is minimal; (2) it presents a large surface area (consistent with the first constraint) to allow for injection of various drugs; (3) it is designed purely and simply for one-way flow, i.e., drug injection is inward only; (4) it is designed so that a variety of drugs may be injected into the peritoneal cavity toward the mesenteric peritoneal membrane; (5) it has a resilient, dome-shaped surface above the receiving reservoir so that the dome may be depressed to expel insulin from the receiving reservoir into the peritoneal cavity; and (6) it is not designed for peritoneal dialysis and, in fact, would not function if used for this purpose. This peritoneal injection catheter has been quite successful for use in administering insulin to diabetic patients; however, in spite of this success, some difficulties have been observed.

The major difficulty has been that this catheter occasionally becomes obstructed after it is implanted in a patient. At present, the chief causes of such catheter obstruction appear to be the accumulation of body cells in the peritoneal opening and tissue growth over or within the peritoneal opening. Such obstruction, of course, interrupts catheter use, and the obstruction may be difficult to remove. Additionally, when attempting to dislodge the obstruction from the peritoneal catheter, the peritoneal catheter may occasionally rupture, thereby necessitating complete removal of the catheter.

The Preferred Embodiments

The peritoneal catheter of the present invention is constructed so as to minimize cellular growth on the peritoneal catheter during use by a patient. The invention is best understood by reference to the drawings wherein like parts are designated with like numerals throughout.

Referring now more particularly to FIG. 1, peritoneal catheter 10 is shown implanted in the abdominal wall 90 of a torso 92 and provides fluid communication from peritoneal catheter 10 with the peritoneal membrane 94 surrounding peritoneal cavity 96. It should be noted that peritoneal cavity 96 is shown somewhat distended as though infused with dialysate, in order to more clearly set forth the environment of peritoneal catheter 10.

Figure 2:
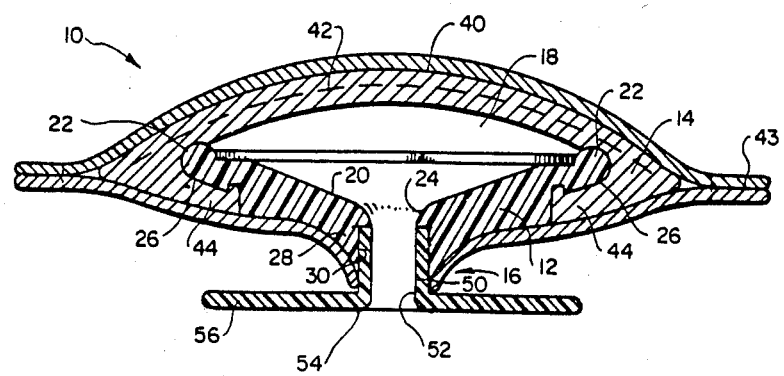
FIG. 2 is a vertical cross-sectional view of one presently preferred embodiment of the present invention.

Referring now more particularly to FIG. 2, one presently preferred embodiment of the peritoneal catheter apparatus of this invention, designated generally as 10, includes a body 12, a cap 14, and a stem 16. Body 12 serves as the basal member for peritoneal catheter 10 and is configured with a funnel-like section 20 having a relatively shallow depth in comparison with the relatively enlarged diameter. The depth of funnel section 20 is selectively predetermined so as to contain a predetermined body of insulin which may be suitably retained momentarily or expelled, as desired.

Funnnel section 20 is surrounded at its upper edge by an upstanding rim 22 and terminates downwardly toward its center in a throat 24. Body 12 is fabricated from a suitable, puncture resistant plastic material such as, for example, a conventional, biocompatible polyurethane. Body 12 is also provided with sufficient thickness so as to preclude inadvertent puncture by a needle.

The opposite edge of rim 22 is formed as a retainer shelf 26 for the purpose of retaining an edge or lip 44 of cap 14. The lower portion of body 12 includes a neck 28 having a coaxial counterbore 30. The internal diameter of counterbore 30 is selectively predetermined so that column 50 may be telescopically received into abutment with throat 24, as will be set forth more fully below.

Cap 14 is configured with an outwardly curved dome-like puncture zone shown as dome 40. The outer circumference of cap 14 includes an inwardly directed circumferential lip 44 adapted to be received in snap-fit relationship with shelf 26 for the purpose of mounting cap 14 to body 12. The height of rim 22, as well as the diameter and the depth of funnel section 20 in combination with the hemispherical radius of cap 14, selectively predetermine the volume of the resulting receiving reservoir 18.

Cap 14 is fabricated from a suitable biocompatible material (such as silicone rubber) having the desired characteristics of being: (a) resilient, (b) readily penetrable, and (c) resealable to accommodate being flexed and punctured numerous times without degradation of the structural integrity of cap 14. A reinforcing material 42 is preferably embedded in the biocompatible material of cap 14. Also, a portion of cap 14 and body 12 may be covered with a suitable, biocompatible velour material 43 to accommodate tissue ingrowth.

Stem 16 is configured as a hollow tubular column 50 having a hollow lumen 52 extending therethrough. As previously mentioned, stem 16 is telescopically received into abutment throat 24. The diameter of lumen 52 matches the diameter of throat 24 so as to provide a continuous, smooth flow channel through peritoneal catheter 10.

The distal end 54 of tubular column 50 is provided with a diametrically enlarged flange 56. As shown, flange 56 is located immediately adjacent distal end 54 of tubular column 50. Thus, flange 56 is adapted to rest against peritoneal membrane 54, as will be described more fully below.

In use, peritoneal catheter 10 is first surgically implanted in a patient. This is accomplished by making an incision in the patient's abdominal wall 90 and peritoneal membrane 94 (see FIG. 1). The peritoneal catheter is then placed in the patient such that distal end 54 of stem 16 extends into peritoneal cavity 96 with flange 56 being against peritoneal membrane 94. Peritoneal catheter 10 is then secured in place by means of sutures.

Once peritoneal catheter 10 is in place, the user injects insulin into receiving reservoir 18 by penetrating dome 40 with a conventional, hollow needle. Advantageously, the insulin in receiving reservoir 18 may be allowed to slowly percolate through lumen 52 into peritoneal cavity 96 or, upon demand, the user may depress dome 40 with a finger to forceably expel insulin from receiving reservoir 18 through lumen 52 into peritoneal cavity 96.

Figure 3:
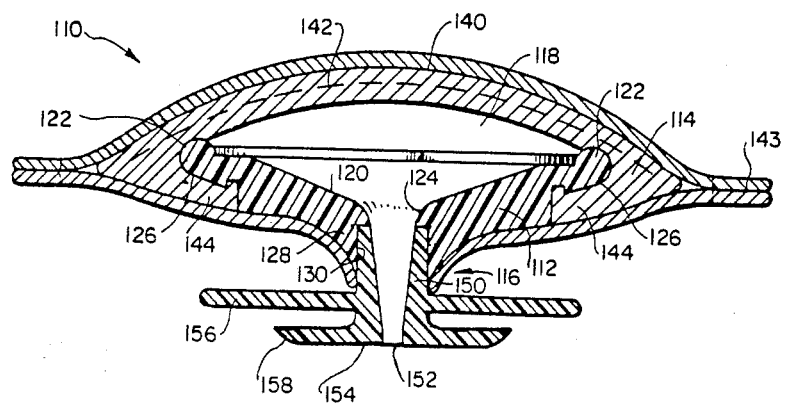
FIG. 3 is a vertical cross-sectional view of a second preferred embodiment of the present invention.

A second preferred embodiment of a peritoneal catheter is FIG. 3. Significantly, the second is configured so as to geometrically help minimize catheter obstruction. As with the first embodiment, this embodiment also includes a body 112, a cap 114, and a stem 116. The body 112 and the cap 114 of this embodiment are in all respects identical to those described in connection with the first embodiment. However, the distal end of tubular column 150 is configured somewhat differently. As shown, the distal end 154 of tubular column 150 is provided with two, diametrally enlarged flanges 156 and 158. As shown, flange 158 is somewhat smaller than flange 156 and is located immediately adjacent distal end 154 of tubular column 150. Advantageously, the outer edges of flange 158 are somewhat rounded, as shown, such that flange 158 has no sharp edges which could injure adjacent tissue.

Tubular column 150, together with flanges 156 and 158, may be formed as a single unit, as shown. Alternatively, tubular column 150 and flange 156 may be formed as a single unit, with flange 158 being attached to a smaller tubular column which is adapted to be snugly received within lumen 152.

Peritoneal catheter 110 is surgically implanted in a patient in exactly the same manner as the first embodiment, with the flange 156 resting against the peritoneal membrane 94 (see FIG. 1). However, in the event that body tissue or cells should begin to grow or accumulate adjacent flange 156 of peritoneal catheter 110, the cells would grow along the surface of flange 156 so as to grow into the space between flange 156 and flange 158. Thereafter, the tissue would be forced to double back on itself in order to continue its growth. It is well known that, unless the growth is cancerous, cell growth will cease as soon as the tissue doubles back on itself. In any event, it is highly unlikely that the cells would thereafter grow outward and upward over the top flange 158, thereby occluding the distal end of 154 of tubular column 150.

In order to minimize the adhesion and accumulation of body cells and tissues on the peritoneal catheter, it has been found desirable to form or cover those portions of the peritoneal catheter which are located within the peritoneum with a material to which cells and body tissues do not readily adhere.

Such materials may be used to form or cover those portions of the catheter which are immediately adjacent the distal opening of the tubular column. In particular, these materials which inhibit cellular adhesion could be used on all or part of the diametrically enlarged flanges which are located within the peritoneal cavity. Hence, in the embodiment of FIG. 2, it may be desirable to construct or coat tubular column 50 and flange 56 with such cellular adhesion-resistant materials; in the embodiment of FIG. 3, tubular column 150 and flanges 156 and 158 would be constructed or coated with such materials.

As discussed above, the tubular column and flanges are preferably constructed of a polyurethane material because of the rigidity, structural integrity, and relative biocompatibility of polyurethane. However, cell adhesion and accumulation can be a problem when polyurethane is used as the polymer for a device placed within the peritoneal cavity.

Materials which may be used to minimize cellular adhesion and accumulation are generally hydrogels or other surface modifying materials which decrease the aqueous interfacial energies. These materials include both synthetic and naturally occurring polymers, as well as materials such as pyrolytic carbon. Among the synthetic polymers are poly(ethylene glycol), poly(vinyl pyrrolidone), polyacrylated hydrogels, poly(hydroxyethyl methacrylate), and poly(vinyl alcohol). Naturally occurring polymers which may be utilized to minimize cellular adhesion include agarose and crosslinked dextrans.

Since the mechanical strengths of these materials are generally small, it is preferable to combine these materials with a base polymer, or to apply these materials to a preformed material, which has the required mechanical characteristics.

Accordingly, that portion of the peritoneal catheter which is subjected to potential cellular adhesion and accumulation may be constructed of a combination of polymers—one having a sufficient mechanical structural integrity (such as polyurethane), and the second polymer being one which inhibits cellular adhesion and accumulation (such as one of the foregoing synthetic or naturally occurring polymers). If a portion of the peritoneal catheter is constructed of such a combination of polymers, the polymer which inhibits cellular adhesion may comprise up to about twenty percent (20%) of the combination of polymers. However it will be appreciated that depending upon the polymers used, cross-linking agents may have to be added in order to produce the necessary rigidity and structural integrity. By incorporating the cellular adhesion resistant polymer into the polymeric network of the base polymer which provides structural integrity, the surface can possess the quality necessary to resist cellular adhesion.

Alternatively, and presently preferred, those portions of the peritoneal catheter which are subjected to potential cellular adhesion are preferably coated with a polymer which will minimize such cellular adhesion and accumulation. In order to achieve bonding of this coating to the base polymer of the catheter, a variety of methods can be utilized; for example, irradiation grafting, creating an interpenetrating network, or incorporating reactive groups into the base polymer so as to covalently bond to the hydrogel.

In one presently preferred embodiment of the present invention, a coating solution is made by combining a polyurethane polymer and a poly(ethylene glycol) polymer in a suitable solvent; dimethyl acetimide ("DMAC") is a solvent which is suitable for dissolving both polyurethane and poly(ethylene glycol). It has been found that when the DMAC solvent forms from about ninety percent (90%) to about 95 percent (95%) of the solution, a thick syrupy solution results. The polyurethane and poly(ethylene glycol) are preferably in about equal proportions. This thick solution can be readily used to coat the desired portions of the peritoneal catheter.

While the thickness of the solution can be varied to allow for either a relatively thin or thick coat to be formed, it must be remembered that the opening through the tubular column must remain patent. Thus, if a thick coating is desired, it is preferable to double or triple coat in order to provide even coating without clogging the tubular column. In the presently preferred embodiments, it has been found that a coating in the range of from about 0.005 inch to about 0.01 inch form a satisfactory layer to accomplish the desired result.

In the coating solution, the DMAC not only acts as a solvent, but it also acts to swell the polyurethane in the peritoneal catheter. Thus, the polyurethane in the coating acts to form an interpenetrating network with the polyurethane of the peritoneal catheter so as to allow the coating to be securely adhered to the base polymer. In addition, there is also some hydrogen bonding between the polyurethane components of the coating and the polyurethane components of the peritoneal catheter. The combination of this bonding and the interpenetrating network is that the coating is securely affixed to the peritoneal catheter.

In the embodiment discussed above, poly(ethylene glycol) is hydrophilic, while polyurethane is relatively hydrophobic. Since the peritoneal catheter is utilized in an aqueous condition, the poly(ethylene glycol) portion of the coating more dominantly presents itself to the cells in the peritoneal cavity; thus, the body cells are attracted to the poly(ethylene glycol). Because of the cellular adhesion resistance of the poly(ethylene glycol), the cells do not attach or adhere to the poly(ethylene glycol). Moreover, the cells do not adhere to the polyurethane because the hydrophilic nature of the poly(ethylene glycol) makes it more predominant in the exposure to the body cells.

The other synthetic and naturally occurring polymers which are mentioned above are materials which are capable of minimizing cellular adhesion. These polymers can be applied by dissolving them in a suitable solvent with polyurethane (or other base polymer of the catheter) and by coating the peritoneal catheter with the resultant solution. Of course, it will be appreciated that when the naturally occurring polymers are used, as well as polyvinyl alcohol, crosslinking additives must be added to the solution in order to preclude dissolving of the coating in the aqueous state present in the peritoneal cavity.

In another embodiment within the scope of the present invention, a coating of pyrolytic carbon is applied to the base polymer of the peritoneal catheter. This is most easily done through a plasma deposition process wherein the pyrolytic carbon is electrically charged in order to securely attach it to the base polymer. The resultant "glassy" finish to the peritoneal catheter minimizes cellular adhesion to the catheter and the accumulation of cells and tissue on the surfaces of the catheter.

In still another embodiment within the scope of the present invention, the base polymer (such as polyurethane) is irradiated with high energy radiation, such as gamma rays or ultra-violet radiation, to form active sites on the surface of the base polymers. By simultaneously, exposing these active sites to a cell-resistant polymer, such as poly(ethylene glycol) or polyvinyl pyrrolidone), the monomeric forms of the cell-resistant polymers can be grafted to the base polymer.

In a further embodiment within the scope of the present invention, reactive groups (such as peroxide groups) may be incorporated into the base polymer so that they can covalently bond to a cell-resistant polymer such as poly(ethylene glycol) or poly(vinyl pyrrolidone).

In light of the foregoing, it can be appreciated that the novel peritoneal injection catheter and the embodiments described above minimize the adhesion and accumulation of cells on the surface of the peritoneal catheter. This improved peritoneal injection catheter also minimizes tissue growth on the surfaces of the peritoneal catheter. Further, this invention comprises a method for minimizing such cellular adhesion, while still maintaining the structural integrity of the peritoneal catheter. The result is an improved implantable subcutaneous peritoneal injection catheter which may be used by a single patient over a relatively long period of time without interruption or malfunction.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A subcutaneously implantable injection conduit for injecting a drug into a peritoneal cavity, comprising:
   a hollow receptacle for receiving the drug, the hollow receptacle having a penetrable portion;
   a hollow stem having a proximal end and a distal end, the proximal end of the stem being attached to the receptacle such that the stem forms a passageway extending from the chamber;
   a diametrally enlarged flange attached to the stem such that, when the conduit is implanted under a layer of skin adjacent the peritoneal cavity and the flange is secured adjacent the parietal peritoneal membrane, the distal end of the hollow stem is positioned within the peritoneal cavity; and
   means for inhibiting cellular adhesion comprising a material coating on at least a portion of the conduit.

2. A subcutaneously implantable injection conduit as defined in claim 1 wherein the means for inhibiting cellular adhesion comprises a material covering the enlarged flange.

3. A subcutaneously implantable injection conduit as defined in claim 2 wherein the material includes poly(ethylene glycol).

4. A subcutaneously implantable injection conduit as defined in claim 2 wherein the material includes poly(vinyl pyrrolidone).

5. A subcutaneously implantable injection conduit as defined in claim 2 wherein the material includes pyrolytic carbon.

6. A subcutaneously implantable injection conduit as defined in claim 2 wherein the material includes a polyacrylated hydrogel.

7. A subcutaneously implantable injection conduit as defined in claim 2 wherein the material includes poly(hydroxyethyl methacrylate).

8. A subcutaneously implantable injection conduit as defined in claim 2 wherein the material includes poly(vinyl alcohol).

9. A subcutaneously implantable injection conduit as defined in claim 2 wherein the material includes agarose.

10. A subcutaneously implantable injection conduit as defined in claim 2 wherein the material includes cross-linked dextrans.

11. A subcutaneously implantable injection conduit for injecting a drug into a peritoneal cavity, comprising:
    a hollow receptacle for receiving the drug, the hollow receptacle having a penetrable portion;
    a hollow stem having a proximal end and a distal end, the proximal end of the stem being attached to the receptacle such that the stem forms a passageway extending from the chamber;
    a diametrally enlarged flange attached to the stem such that, when the conduit is implanted under a layer of skin adjacent the peritoneal cavity and the flange is secured adjacent the parietal peritoneal membrane, the distal end of the hollow stem is positioned within the peritoneal cavity, said flange being comprised of a material capable of inhibiting cellular adhesion on the surface of the flange.

12. A subcutaneously implantable injection conduit as defined in claim 11 wherein the material for inhibiting cellular adhesion includes poly(ethylene glycol).

13. A subcutaneously implantable injection conduit as defined in claim 11 wherein the material for inhibiting cellular adhesion includes poly(vinyl pyrrolidone).

14. A subcutaneously implantable injection conduit as defined in claim 11 wherein the material for inhibiting cellular adhesion includes pyrolytic carbon.

15. A subcutaneously implantable injection conduit as defined in claim 11 wherein the material for inhibiting cellular adhesion includes a polyacrylated hydrogel.

16. A subcutaneously implantable injection conduit as defined in claim 11 wherein the material for inhibiting cellular adhesion includes poly(hydroxyethyl methacrylate).

17. A subcutaneously implantable injection conduit as defined in claim 11 wherein the material for inhibiting cellular adhesion includes poly(vinyl alcohol).

18. A subcutaneously implantable injection conduit as defined in claim 11 wherein the material for inhibiting cellular adhesion includes agarose.

19. A subcutaneously implantable injection conduit as defined in claim 11 wherein the material for inhibiting cellular adhesion includes cross-linked dextrans.

20. A subcutaneously implantable injection conduit for injecting a drug into a peritoneal cavity, comprising:
    an injection receiver having a diametrally enlarged, convergent receiving surface and an opening in the receiving surface;
    a diametrally enlarged, penetrable cover across the receiving surface in spaced relationship therewith, the cover forming a receiving reservoir in combination with the receiving surface;
    a hollow stem having a proximal end and a distal end, the proximal end of the stem being attached to the injection receiver such that the stem forms a passageway extending from the opening in the receiving surface, the stem having a length sufficient that the stem penetrates the parietal peritoneal membrane and extends into the peritoneal cavity;
    a first diametrally enlarged flange attached to the stem such that, when the conduit is implanted under a layer of skin adjacent the peritoneal cavity and the first flange is secured adjacent the parietal peritoneal membrane, the distal end of the hollow stem is directed toward the mesenteric peritoneal membrane;
    a second diametrally enlarged flange, said second flange being attached to the stem in spaced relationship with the first flange; and
    a coating applied to the first and second enlarged flanges, and to the hollow stem, said coat being capable of inhibiting cellular adhesion to surfaces of the first and second flanges, and the hollow stem.

21. A subcutaneously implantable injection conduit as defined in claim 20 wherein the material for inhibiting cellular adhesion includes poly(ethylene glycol).

22. A subcutaneously implantable injection conduit as defined in claim 20 wherein the material for inhibiting cellular adhesion includes poly(vinyl pyrrolidone).

23. A subcutaneously implantable injection conduit as defined in claim 20 wherein the material for inhibiting cellular adhesion includes pyrolytic carbon.

24. A subcutaneously implantable injection conduit as defined in claim 20 wherein the material for inhibiting cellular adhesion includes a polyacrylated hydrogel.

25. A subcutaneously implantable injection conduit as defined in claim 20 wherein the material for inhibiting cellular adhesion includes poly(hydroxyethyl methacrylate).

26. A subcutaneously implantable injection conduit as defined in claim 20 wherein the material for inhibiting cellular adhestion includes poly(vinyl alcohol).

27. A subcutaneously implantable injection conduit as defined in claim 20 wherein the material for inhibiting cellular adhesion includes agarose.

28. A subcutaneously implantable injection conduit as defined in claim 20 wherein the material for inhibiting cellular adhesion includes cross-linked dextrans.

29. A method for manufacturing a peritoneal injection catheter, the method comprising the steps of:
   obtaining an injection conduit, comprising:
      a shallow vessel having a penetrable membrane;
      a hollow stem having a proximal end and a distal end, the proximal end of the stem being attached to the vessel such that the stem forms a passageway extending from the vessel; and
      a diametrally enlarged flange attached to the stem such that, when the conduit is implanted underneath a layer of skin adjacent the peritoneal cavity and the flange is secured adjacent the parietal peritoneal membrane, the distal end of the hollow stem is positioned within the peritoneal cavity; and
   coating the flange and the hollow stem of the injection catheter with a material capable of inhibiting cellular adhesion on the surfaces of the flange and the hollow stem.

30. A method for manufacturing a peritoneal injection catheter as defined in claim 29 where the coating includes poly(ethylene glycol).

31. A method for manufacturing a peritoneal injection catheter, the method comprising the steps of:
   obtaining an injection conduit, comprising:
      a shallow vessel having a penetrable membrane;
      a hollow stem having a proximal end and a distal end, the proximal end of the stem being attached to the vessel such that the stem forms a passageway extending from the vessel; and
      a diametrally enlarged flange attached to the stem such that, when the conduit is implanted underneath a layer of skin adjacent the peritoneal cavity and the flange is secured adjacent the parietal peritoneal membrane, the distal end of the hollow stem is positioned within the peritoneal cavity, said flange being comprised of a polymeric material;
   preparing a solution of the polymeric material from which the flange is comprised and a material capable of inhibiting cellular adhesion in a suitable solvent; and
   coating the flange and the hollow stem of the injection catheter with the solution.

32. A method for manufacturing a peritoneal injection catheter as defined in claim 31 where the solution comprises polyurethane, poly(ethylene glycol), and dimethyl acetimide.

33. A method for minimizing cellular adhesion on a catheter, the method comprising the steps of:
   obtaining an injection conduit, comprising:
      a shallow vessel having a penetrable membrane;
      a hollow stem having a proximal end and a distal end, the proximal end of the stem being attached to the vessel such that the stem forms a passageway extending from the vessel; and
      a diametrally enlarged flange attached to the stem such that, when the conduit is implanted underneath a layer of skin adjacent the peritoneal cavity and the flange is secured adjacent the parietal peritoneal membrane, the distal end of the hollow stem is positioned within the peritoneal cavity;
   coating the flange and the hollow stem of the injection catheter with a material capable of inhibiting cellular adhesion on the surfaces of the flange and the hollow stem; and
   implanting the injection conduit underneath a layer of skin adjacent the peritoneal cavity with the membrane being generally parallel to the skin, the hollow stem penetrating the parietal peritoneal membrane and extending into the peritoneal cavity, the diametrally enlarged flange being secured adjacent the parietal peritoneal membrane, the distal end of the hollow stem being directed toward the mesenteric peritoneal membrane, and the passageway communicating between the vessel and the peritoneal cavity.

* * * * *

UNITED STATES PATENT AND TRADEMARK OFFICE
CERTIFICATE OF CORRECTION

PATENT NO. : 4,557,724
DATED : December 10, 1985
INVENTOR(S) : DONALD E. GREGONIS et al.

It is certified that error appears in the above-identified patent and that said Letters Patent is hereby corrected as shown below:

Column 1, line 44, "twenty fold" should be --twentyfold--
Column 2, line 29, "qantities" should be --quantities--
Column 6, line 5, "stem. the" should be --stem. The--
Column 6, line 34, "is to provide" should be --to provide--
Column 6, line 49, "invention;" should be --invention; and--
Column 6, line 51, "invention;" should be --invention.--
Column 7, line 18, "conventional" should be --with conventional--
Column 8, line 9, "have" should be --has--
Column 9, line 34, "abutment throat" should be --abutment with throat--
Column 9, line 62, "the second" should be --this second embodiment--
Column 12, lines 41-42, "simultaneously, exposing" should be --simultaneously exposing--

Signed and Sealed this

First Day of April 1986

[SEAL]

Attest:

DONALD J. QUIGG

Attesting Officer

Commissioner of Patents and Trademarks